US009848885B2

(12) United States Patent
Shepard

(10) Patent No.: US 9,848,885 B2
(45) Date of Patent: Dec. 26, 2017

(54) CLIP SYSTEMS FOR TREATING BODY TISSUES

(71) Applicant: Boston Scientific Scimed, Inc., Maple Grove, MN (US)

(72) Inventor: Douglas C. Shepard, Mansfield, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 325 days.

(21) Appl. No.: 14/596,530

(22) Filed: Jan. 14, 2015

(65) Prior Publication Data

US 2015/0201946 A1    Jul. 23, 2015

Related U.S. Application Data

(60) Provisional application No. 61/928,783, filed on Jan. 17, 2014.

(51) Int. Cl.
| | |
|---|---|
| *A61B 17/128* | (2006.01) |
| *A61B 17/122* | (2006.01) |
| *A61B 1/00* | (2006.01) |
| *A61B 17/064* | (2006.01) |
| *A61B 17/068* | (2006.01) |
| *A61B 17/08* | (2006.01) |
| *A61B 17/10* | (2006.01) |
| *A61B 17/00* | (2006.01) |

(52) U.S. Cl.
CPC ...... *A61B 17/1285* (2013.01); *A61B 1/00131* (2013.01); *A61B 17/064* (2013.01); *A61B 17/0682* (2013.01); *A61B 17/083* (2013.01); *A61B 17/10* (2013.01); *A61B 17/122* (2013.01); *A61B 17/1227* (2013.01); *A61B 2017/00296* (2013.01); *A61B 2017/0645* (2013.01)

(58) Field of Classification Search
CPC .............. A61B 17/122; A61B 17/1227; A61B 17/1285; A61B 1/00131; A61B 17/064; A61B 17/0682; A61B 17/083
USPC .............. 1/1; 227/19, 175.1, 176.1; 600/124; 606/108, 139, 140, 142, 144, 151, 158, 606/213, 219, 232
See application file for complete search history.

(56) References Cited

U.S. PATENT DOCUMENTS

| | | | |
|---|---|---|---|
| 5,259,366 A | 11/1993 | Reydel et al. | |
| 5,626,614 A | 5/1997 | Hart | |
| 6,645,205 B2 * | 11/2003 | Ginn | ................. A61B 17/0644 128/200.24 |

(Continued)

*Primary Examiner* — Vy Bui
(74) *Attorney, Agent, or Firm* — Fay Kaplun & Marcin, LLP

(57) ABSTRACT

A device for compressing body tissue includes a clip having a connection portion with first and second clip arms extending therefrom, the clip includes a recess formed on an inner surface of the connection portion, the recess being shaped and sized to slidably receive a mounting bar coupled to an outer surface of an endoscope on which the mounting bar is mounted with inner surfaces of the first and second clip arms maintained in an open position by contact between an endoscope on which the mounting bar is mounted and the inner surfaces of the first and second clip arms. The clip is slidable over the outer surface of an endoscope on which the mounting bar is mounted until the clip moves distally beyond the distal end of the endoscope so that the first and second clip arms spring closed to grip tissue therebetween.

17 Claims, 5 Drawing Sheets

(56) References Cited

U.S. PATENT DOCUMENTS

| | | |
|---|---|---|
| 6,726,704 B1 | 4/2004 | Loshakove et al. |
| 7,905,893 B2 | 3/2011 | Kuhns et al. |
| 9,301,754 B2 * | 4/2016 | Duncan .............. A61B 17/0057 |
| 2011/0208210 A1 | 8/2011 | Baur et al. |
| 2012/0209297 A1 | 8/2012 | Juggenheimer et al. |
| 2015/0238194 A1 | 8/2015 | Kuhns et al. |

\* cited by examiner

CLIP SYSTEMS FOR TREATING BODY TISSUES

CROSS-REFERENCE TO RELATED PATENT APPLICATIONS

This application claims priority to U.S. Provisional Patent Application Ser. No. 61/928,783, entitled "Clip Systems for Treating Body Tissues" and filed Jan. 17, 2014, which is incorporated herein by reference in its entirety.

BACKGROUND

The present disclosure relates to systems and methods for treating body tissues, more particularly to clip systems and methods for compressing body tissues.

Surgical clips are generally used during a variety of medical procedures, such as, for holding or clamping body tissues together, squeezing blood vessels or other bodily lumens to prevent bleeding, and so on. Clips may be introduced within a patient's body using various approaches such as subcutaneous approach and minimally invasive approach. In a subcutaneous approach, skin of the patient may be penetrated to enter a body lumen to clamp a clip about a target treatment site for closure. In minimally invasive approach, a clip having a pair of arms may be deployed using an endoscope introduced into the patient's body through a natural anatomical body opening such as the mouth.

Certain treatments require the deployment of multiple clips within the body. Many conventional systems deliver only one clip at a time and must be removed from the body to load a new clip which may then be delivered to a second target treatment site with this process repeated until the desired number of clips has been deployed. As a result, the deployment of multiple clips is complicated, time consuming and expensive.

SUMMARY

One embodiment includes a system for compressing body tissue. The system includes a mounting bar, a clip, and a control member. The mounting bar includes a coupling structure for mounting the mounting bar on an endoscope so that the mounting bar extends along a portion of a distal end of an endoscope with the mounting bar mounted parallel to a longitudinal axis of the endoscope. The clip has a connection portion with first and second clip arms extending therefrom. An inner surface of the connection portion includes a recess shaped and sized to slidably receive the mounting bar while inner surfaces of the first and second clip arms are maintained in an open position by contact with the endoscope. The control member is coupled to the clip to move the clip along the mounting bar until the clip moves distally beyond the distal end of an endoscope permitting the first and second clip arms to spring close and grip tissue received therebetween.

Another embodiment includes a device for compressing body tissue. The device includes a clip having a connection portion with first and second clip arms extending therefrom. An inner surface of the connection portion includes a recess shaped and sized to slidably receive a mounting bar coupled to an outer surface of an endoscope on which the mounting bar is mounted. Inner surfaces of the first and second clip arms are maintained in an open position by contact with the endoscope. The clip is slidable over the outer surface of an endoscope on which the mounting bar is mounted until the clip moves distally beyond the distal end of the endoscope so that the first and second clip arms spring close to grip tissue received therebetween.

In yet another embodiment is a method for compressing body tissue. The method includes advancing an endoscope on which a mounting bar is mounted to a target site in a living body. The endoscope on which the mounting bar is mounted being fitted with a plurality of clips mounted over an outer surface thereof. Each clip has a connection portion with first and second clip arms extending therefrom. Each clip includes a recess on an inner surface of the connection portion that is shaped and sized to slidably receive the mounting bar so that an outer surface of the endoscope maintains the inner surfaces of the first and second clip arms separated from one another in an open position. The method further includes drawing a tissue into the endoscope and actuating a control member to slide a distalmost one of the clips distally beyond the distal end of the endoscope and the mounting bar so that the first and second clip arms spring closed to grip the tissue drawn into the endoscope.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts.

Embodiments of the present disclosure relate to systems and methods for compressing body tissues. A system is configured to receive and deploy multiple clips to the body tissues without removing the system from the body. The system includes a mounting bar mounted over an endoscope, a clip including a connection portion with first and second clip arms extending therefrom, and a control member coupled to the clip. The mounting bar extends along a distal portion of the endoscope parallel to a longitudinal axis of the endoscope. The clip includes a recess formed on an inner surface of the connection portion that is shaped and sized to slidably receive the mounting bar with inner surfaces of the first and second clip arms maintained in an open position by contact between an endoscope and the inner surfaces of the first and second clip arms. The control member includes a pusher and a wire distally coupled to the pusher. The pusher is in communication with the clips to advance the clips along the mounting bar until a distalmost clip moves distally beyond the distal end of the endoscope and the mounting bar so that the first and second clip arms spring close to grip body tissues therebetween.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

Figure 1:
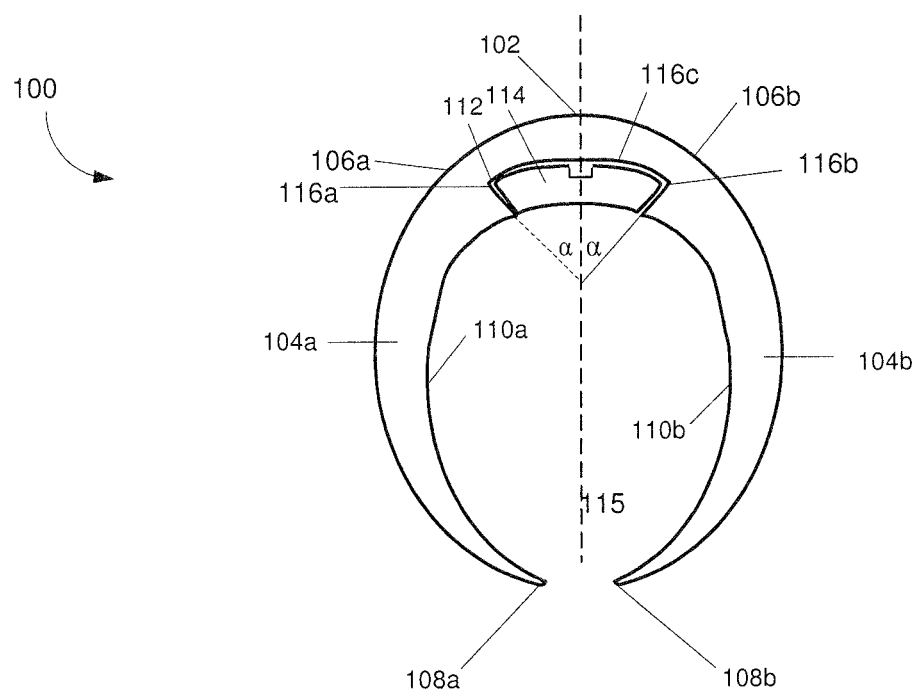
FIG. 1 is a schematic side view of a first exemplary embodiment of a clip in an expanded configuration.

FIG. 1 is a schematic side view of a first exemplary embodiment of a clip 100 in an expanded configuration. The clip 100 includes a connection portion 102 having a first clip arm 104a and a second clip arm 104b. The connection portion 102 of each clip 100 provides a base for extending the clip arms 104a, 104b and includes a recess 112 sized and shaped to receive a mounting bar 114. The first and the second clip arms 104a, 104b have respective first ends 106a and 106b. The first ends 106a, 106b extend to respective free ends 108a, 108b of the clip arms 104a, 104b, which are restrictively elastic about the first ends 106 so that the clip 100 is biased toward a gripping configuration in which the free ends 108a and 108b are drawn against one another. When mounted on an endoscope, the arms 104a and 104b are maintained in an open configuration separated from one another by the body of the endoscope which is received therebetween. The clip arms 104a, 104b are biased to move radially inwards such that a first free end 108a of the first clip arm 104a may come in contact with or substantially close to a second free end 108b of the second clip arm 104b. The thickness of the first ends 106 of the clip arms 104a, 104b of each of the clips 100 in this embodiment is greater than that of the free ends 108 to strengthen the clips arms 104 and to enhance the bias toward the gripping configuration. For instance, the greater thickness of the first ends 106 of the clip arms 104a, 104b applies a regressing force on the clip arms 104a, 104b to bias the clip arms 104a, 104b toward the gripping configuration in the absence of any external stimulus. The clip arms 106a, 106b may be configured in various shapes including, but not limiting to, triangular, irregular, and so on. In the shown example, the clip arms 104a, 104b are shaped as part of a crescent extending from the respective first ends 106 to the free ends 108. In an exemplary embodiment, a thickness of the clip at the connection portion 102 is greater than a thickness at the free ends 108a, 108b to aid in flexibility of the first and second arms 104a, 104b, wherein the thickness may be selected to conform to the required flexibility for a particular application of the clip 100, as those skilled in the art will understand.

The first and second clip arms 104a, 104b, respectively, define a first inner surface 110a and a second inner surface 110b, respectively. The inner surfaces 110a, 110b are shaped to correspond to correspond to a shape of an outer surface of an endoscope on which they are to be mounted (not shown). For example, the inner surfaces 110 of the clip arms 104a, 104b may form a portion of an arc of a circle having a diameter equal to an outer diameter of a circular endoscope on which they are to be mounted. The inner surfaces 110 or portions thereof, such as the inner surface 110a of first clip arm 104a, may be treated with any suitable biocompatible substance known in the art to increase friction between the clip arms 104a, 104b and the received endoscope. In some embodiments, the inner surfaces 110 may include protrusions, indentations, corrugations, or similar micro patterns using different chemical and mechanical techniques known in the art to enhance frictional engagement with the body. In another embodiment, the inner surfaces 110 or portions thereof may be treated to decrease friction between the clip arms 104a, 104b and the endoscope to, for example, aid in deployment of the clips 100 from the endoscope. The inner surfaces 110 may be configured to enhance friction in a manner selected to promote optimal retention of the clips 100 thereon, promoting optimal deployment of the clips 100 off the endoscope while preventing the impeding of deployment of the clips 100 from the endoscope and aiding in retention of the clips 100 at a target tissue site after deployment. For example, the inner surfaces 110 may have abutments and/or grooves that fit into corresponding grooves and/or abutments on the outer surface of the endoscope. In addition, the clip arms 104a, 104b are configured to have a spring constant selected so that the clip arms 104a, 104b are urged radially inward toward one another to maintain frictional engagement with the endoscope. Further, outer surfaces of the clip arms 104a, 104b may optionally be covered with a drug coating, which may be a blend of a drug such as pentoxifylline (PTX) and an excipient, for example, lopromide. However, the drug coating may be a combination of any suitable drug and excipient based on the intended therapeutic effect and the region of treatment.

The clip 100 further includes a recess 112 formed on an inner surface of the connection portion 102. The recess 112 may be shaped and sized to receive a mounting bar 114 that may be removably coupled to the outer surface of the endoscope. The lower surface of the mounting bar 114 may be formed with a curvature conforming to a curvature of the endoscope on which the mounting bar 114 is to be mounted.

The recess 112 includes a first wall 116a, a second wall 116b, and a third wall 116c. The third wall 116c extends between the first and the second walls 116a, 116b. The walls 116a, 116b, 116c may have different orientations so that the recess 112 has a suitable cross-sectional shape including, but not limited to, oval, circular, and T-shape conforming to a cross-sectional shape of the mounting bar 114. In a first embodiment, as shown, the first wall 116a and the second wall 116b may extend into the connection portion 102 at opposing angles. The third wall 116c may be planar and curved to receive a substantially curved mounting bar 114. The curvature of the curved third wall 116c corresponds to a curvature of the inner surface of the connection portion 102. In one embodiment, the walls 116a, 116b may enclose an angle $\alpha$ of approximately 20-60° with an axis 115, wherein the axis 115 bisects the clip 100, as shown in FIG. 1. It is noted, however, that other angles are also envisioned within the scope of the invention. Page: 7

Figure 2:
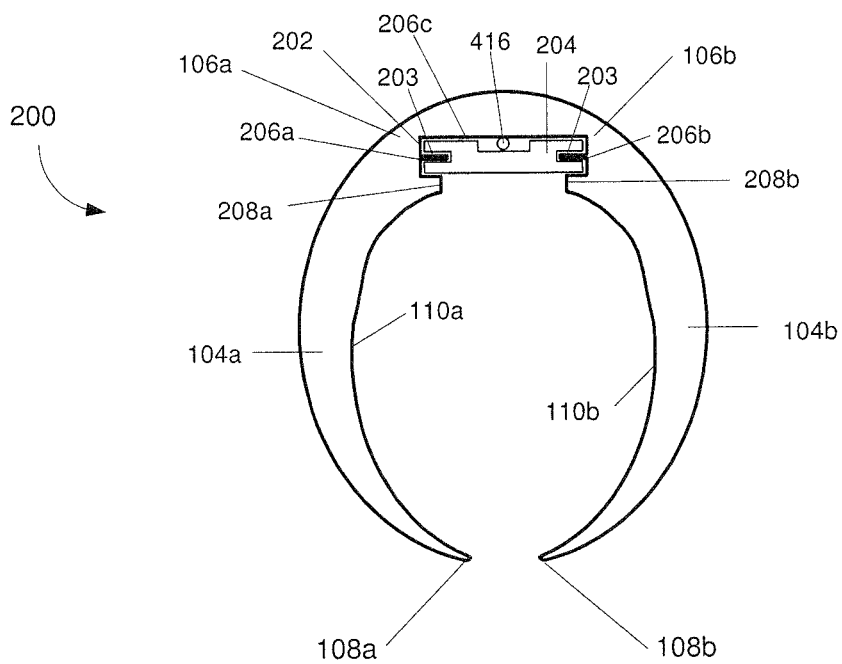
FIG. 2 is a schematic side view of a second exemplary embodiment of a clip in an expanded configuration.
Figure 6:
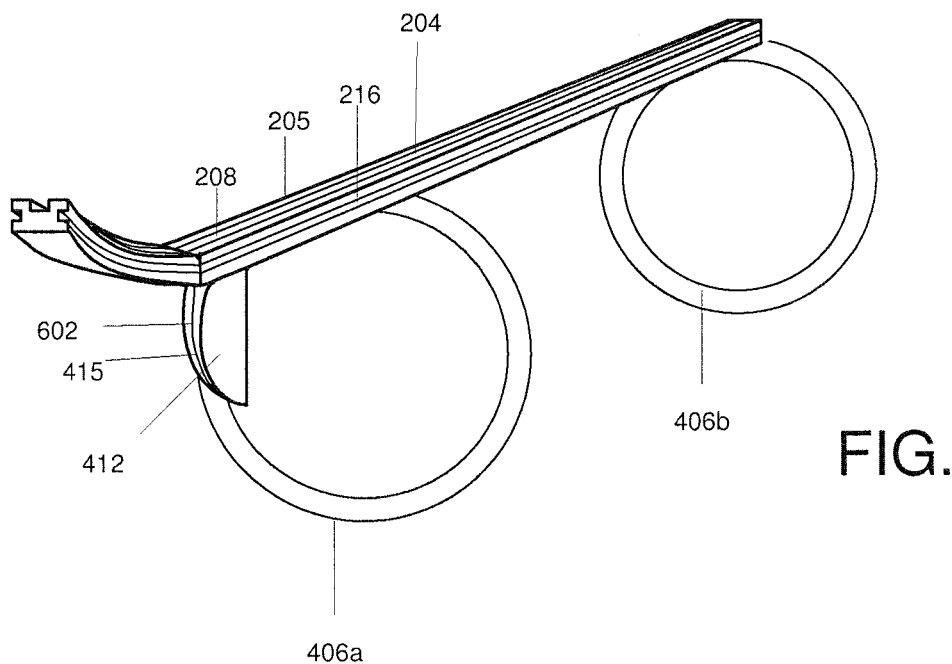
FIG. 6 is a schematic view of an exemplary mounting bar of the clip system of FIGS. 4 and 5.
Figure 7:
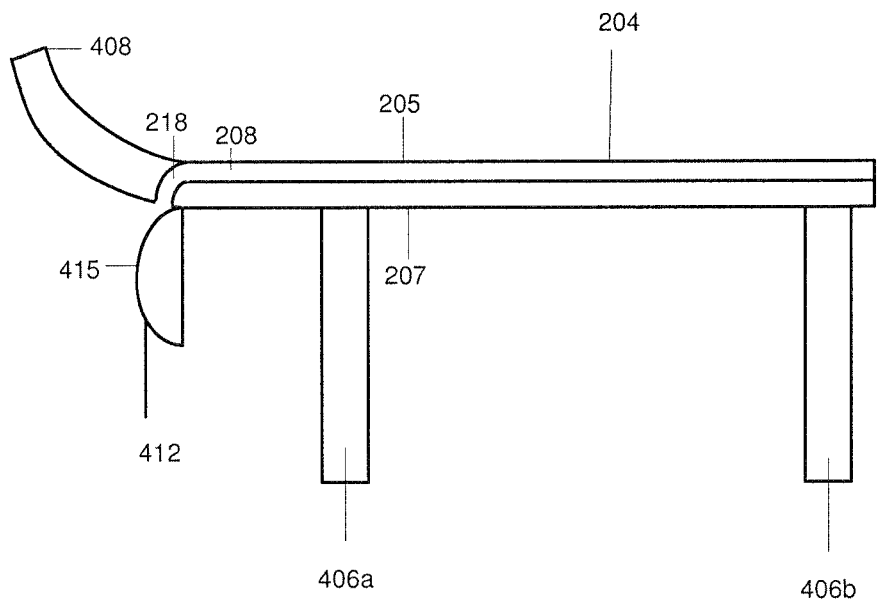
FIG. 7 is a partial cross-sectional side view of the mounting bar of FIG. 6.
Figure 8:
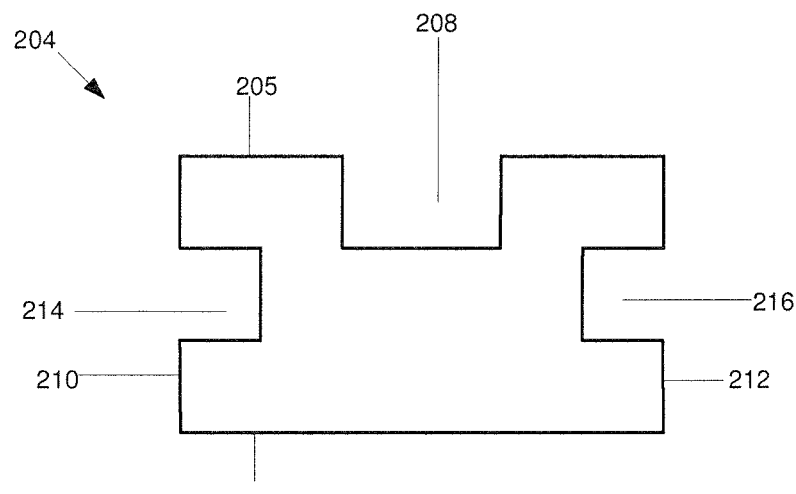
FIG. 8 is a cross-sectional view of the mounting bar of FIG. 6.

As shown in FIG. 2, a clip 200 according to a second embodiment has components similar to those for the clip 100 and these corresponding components are given the same numbers as mentioned in regard to the clip 100 of FIG. 1. These components include the connection portion 102, the clip arms 104a, 104b having first ends 106, free ends 108, and inner surfaces 110. The components individually operate in a manner substantially the same as that described in the description of the clip 100 of FIG. 1. In contrast to the clip 100, a recess 202 of the clip 200 is configured to receive a mounting bar 204, as shown in greater detail in FIGS. 6-8. The recess 202 includes a first wall 206a and a second wall 206b, both substantially perpendicular to a third wall 206c that is substantially parallel and corresponds to the inner surface of the connection portion 102. The recess 202 further includes shoulder portions 208a, 208b axially separating the recess 202 from the inner surfaces 110a, 110b. Thus, the recess 202 is axially separated from a cavity enclosed by the first and second clip arms 104a, 104b. The shoulder portions 208a, 208b maintain the clip 200 on the mounting bar 204 so that the clip 200 cannot be separated from the mounting bar 204 until the clip 200 is moved distally off the bar 204. Thus, the mounting bar 204 may take any shape and does not need to conform to an outer profile of the endoscope.

The mounting bar 204 is formed with a substantially rectangular cross-section. An upper surface 205 of the mounting bar 204, extending away from the endoscope in an operative configuration, includes a wire channel 208. The wire channel 208 is formed as an axial slot extending into the mounting bar 204 by a depth selected to house a wire 416 therein, as will be described in greater detail later on. In an exemplary embodiment, the wire channel 208 may have a rectangular cross-section, although other cross-sectional shapes are envisioned within the scope of the invention. The wire channel 208 extends from a proximal end 209 of the mounting bar 204 to a distal end 211 aligned with a distal end 405 of an endoscope 404. In one embodiment, the wire channel 208 may be open to the upper surface 205 of the mounting bar 204. In another embodiment (not shown), the wire channel 208 may be enclosed within the mounting bar 204, with openings formed at proximal and distal ends thereof to permit slidable insertion of the wire 416 therethrough. As shown in the partial cross-sectional view of FIG. 7, at the distal end 211, the wire channel 208 is open to a wire lumen 218 which extends through the mounting bar 204 from the upper surface 205 to a lower surface 207. In one embodiment, the wire lumen 218 has a substantially circular cross-section to permit insertion of the wire 416 therethrough. It is noted, however, that any other cross-sectional shape may be used without deviating from the scope of the invention. The wire lumen 218 may follow a curved path from the upper surface 205 at the wire channel 208 to the lower surface 207. In another embodiment (not shown), the wire lumen 218 extends from the upper surface 205 to the lower surface 207 along a path extending perpendicular to a longitudinal axis of the linear portion of the mounting bar 204. In yet another embodiment (not shown), the wire lumen 218 extends along an angle from the upper surface 205 to the lower surface 207. It is noted that although the embodiments are depicted with the wire 416 extending through the mounting bar 204, other paths are envisioned within the scope of the invention. In another embodiment (not shown), the wire 416 may pass between the mounting bar 204 and endoscope 404.

The wire 416 may be made of any suitable biocompatible material sufficiently flexible to pass through the endoscope 404 when it has been passed along a tortuous path to a target site within the body. For example, a flexibility of the wire 416 may be substantially greater than that of the mounting bar 204 and the endoscope 404.

When the mounting bar 204 is mounted to the endoscope 404 in a desired position, the wire lumen 418 is open to a wire track 412 extending over the distal opening of the endoscope 404, the wire track 412 guiding the wire 416 from the mounting bar 204 and into the working channel 418 of the endoscope 404. As shown in FIGS. 4-7, the wire track 412 is a convex block including a rail 602 shaped to guide the wire 416 along a predefined path. In an exemplary embodiment, the wire track 412 is a "D"-shaped member permanently attached to the mounting bar 204 so that a curved face 415 thereof faces distally. In an operative configuration, the curved face 415 provides a pathway guiding the wire 416 over the distal end of the endoscope 404 and into the working channel 418. The rail 602 is formed as an elongated recess extending along the curved face 415 to receive the wire 416 therein. A reduced diameter portion (e.g., a fence or lip) may be positioned over the elongated recess of the rail 602 to prevent the wire 416 from being inadvertently dislodged therefrom. In another embodiment, the rail 602 may be formed as a channel extending through the wire track 412 to guide the wire 416 therethrough and into the endoscope channel 418.

First and second lateral side walls 210, 212 of the mounting bar include first and second side channels 214, 216 extending parallel to a longitudinal axis of the mounting bar 204. The first and second side channels 214, 216 are formed as slots extending into the mounting bar 204 by a depth selected to engage a corresponding pair of intermediate bars 500 positioned between each of the clips 100, as will be described in greater detail below. First and second walls 206a, 206b of the recess 202 include protrusions 203 sized to be received within the first and second side channels 214, 216 to prevent the intermediate bars 500 from being received therein.

The intermediate bars 500 are slidably received within the first and second side channels 214, 216 and serve to separate the clips 100 from one another by a predetermined distance. This separation allows the clips 100 to be individually deployed without interfering with one another. In an operative configuration, as the clips 100 are slidably advanced along the mounting bar 204, the intermediate bars 500 also slide along the mounting bar 204 to maintain a desired spacing between adjacent ones of the clips 100. After a distalmost one of the clips 100 moves off the mounting bar 100 and is deployed in the body, the intermediate bars 500 are permitted to slide off the first and second side channels 214, 216. The intermediate bars 500 may then be withdrawn from the body using a known retrieval method or, in another embodiment, may be left in situ. The intermediate bars 500 are formed of a flexible biocompatible material.

Figure 4:
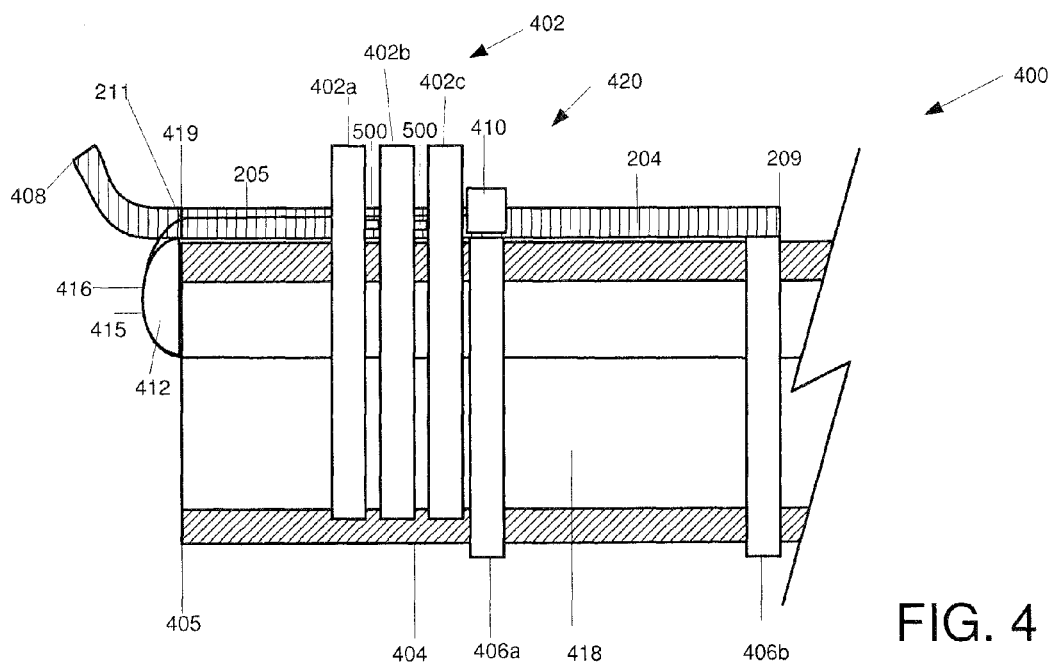
FIGS. 4 and 5 illustrate a mechanism for advancing clips in an exemplary clip system for compressing body tissues.
Figure 5:
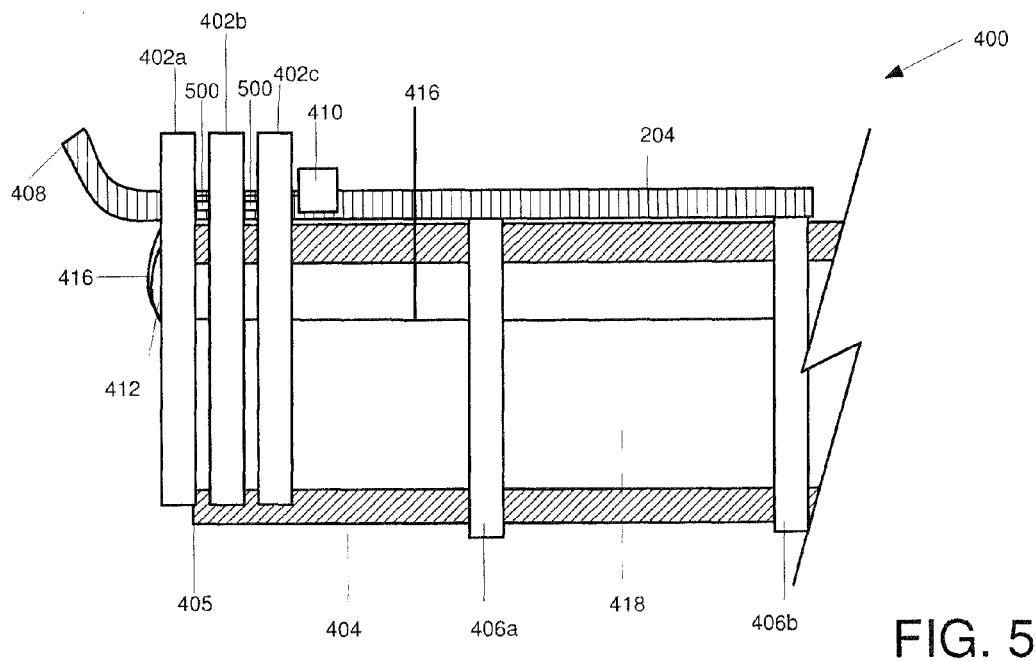
Figure 9:
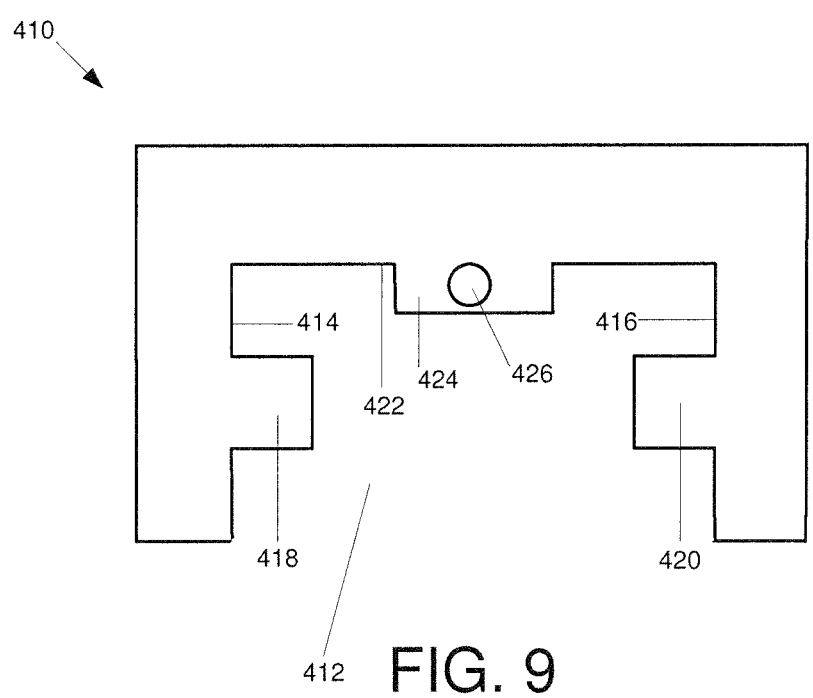
FIG. 9 is a cross-sectional view of the pusher of the clip system of FIGS. 4 and 5.

As shown in FIGS. 4, 5 and 9, the pusher 410 is formed with a rectangular shape having an opening 412 matching an outer profile of the mounting bar 204. Specifically, the opening 412 is substantially rectangular. First and second side walls 414, 416 of the opening 412 include first and second protrusions 418, 420 sized and shaped to engage the intermediate bars 500. Distal movement of the pusher 410 along the mounting bar 204 causes the first and second protrusions 418, 420 to apply a corresponding distal pressure on the intermediate bars 500 to cause distal advancement of the clips 100, as will be described in greater detail with respect to the exemplary method below. An upper wall 422 of the opening 412 comprises a protrusion 424 extending into the opening 412 and sized to slidably engage the wire channel 208. The protrusion 424 includes a wire attachment point 426 receiving a free end of the wire 416. The pusher 410 may engage the mounting bar 204 with a ratcheting engagement so that the pusher is slidable in along the mounting bar 204 in only a distal direction and providing a controlled deployment of the clips off the mounting bar 204.

Figure 3:
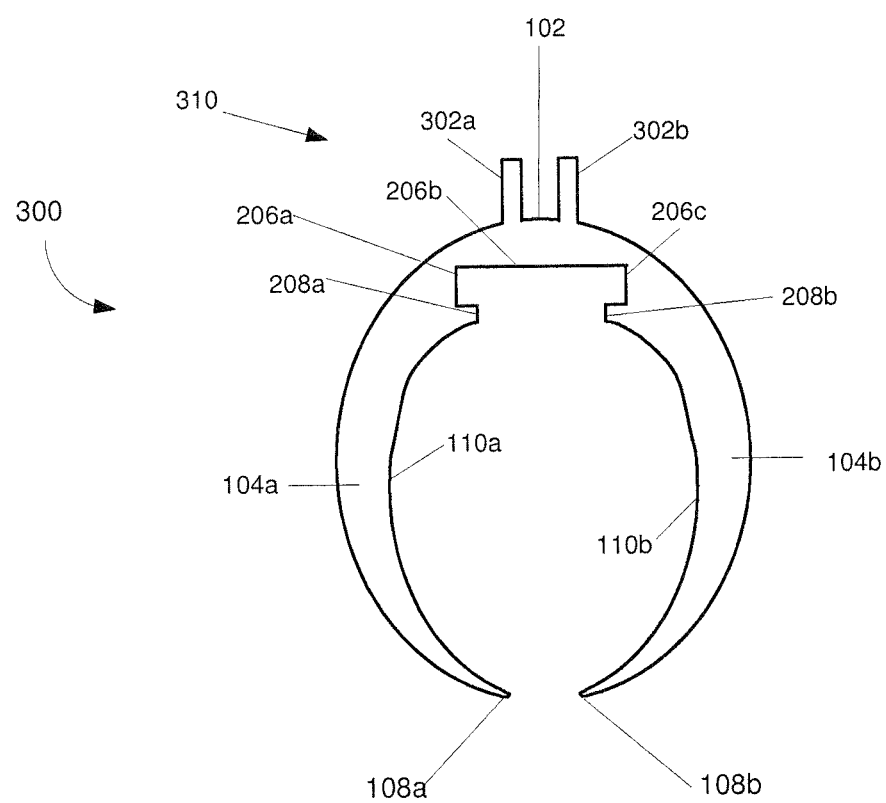
FIG. 3 is a schematic side view of a third exemplary embodiment of a clip in an expanded configuration.

As shown in FIG. 3, a clip 300 according to a third embodiment has components similar to those of the clip 200 shown in FIG. 2 and these corresponding components are given same numbers as mentioned in reference to the clip 200. These components include the connection portion 102, the clip arms 104a, 104b having first ends 106, free ends 108, and inner surfaces 110, the recess 202, the walls 206, and the shoulder portions 208a, 208b. The components individually operate in a manner substantially the same as that described in regard to the clips 100 and 200 of FIGS. 1 and 2. The clip 300 includes a secondary spring structure 310 extending radially outward from the connection portion 102 (i.e., in a direction away from an endoscope on which the clip 300 is mounted). The secondary spring structure includes a first extension arm 302a and a second extension arm 302b. In some embodiments, both the extension arms 302a, 302b are substantially parallel to one another. The extension arms 302a, 302b are suitably rigid to apply an additional biasing force to the clip arms 104a, 104b when the clip 300 is in the expanded configuration urging the clip 300 toward the gripping configuration. The extension arms 302a, 302b may also be drawn toward one another to draw the clip arms 104a and 104b apart from one another to move the clip 300 to the open configuration. However, those of skill in the art will understand that the extension arms 302a, 302b may be arranged in any suitable orientation or angle to desirably alter the strength of the force biasing the clip 300 toward the gripping configuration. The extension arms 302a, 302b according to the invention may provide an additional spring biasing force to retain the clip 300 over the tissue in an operative configuration.

As shown in FIGS. 4 and 5 a clip system 400 includes a mounting bar, such as the mounting bar 204, clips 402a, 402b, 402c (collectively, clips 402), and a control member which includes a pusher 410 and a wire 416, as will be described in greater detail later on. As shown, the mounting bar 204 has a rectangular cross-section, however, other cross-sectional shapes such as, but not limited to, circular, oval, irregular, or the like may also be contemplated. The mounting bar 204 may be suitably shaped and dimensioned to mount over an endoscope 404. The mounting bar 204 is also mounted parallel to a longitudinal axis of the endoscope 404. Further, the mounting bar 204 includes a coupling structure to removably position the mounting bar 204 over a distal portion of the endoscope 404. The coupling structure (FIG. 6) includes locking bands 406a, 406b capable of being coupled or uncoupled to the mounting bar 204. The locking bands 406a, 406b may be circular in shape, though other shapes may be contemplated based on cross-section of an endoscope 404 over which they are to be received. The locking bands 406a, 406b according to this embodiment extend in planes substantially perpendicular to the mounting bar 204 (FIG. 7) so that, when mounted on an endoscope, the locking bands will extend in planes perpendicular to the longitudinal axis of the endoscope. Upon expansion, the locking bands 406a, 406b secure the mounting bar 204 over the distal portion of the endoscope 404.

The mounting bar 204 may be mounted with adjacent ones of the clips 402 being separated from one another by a pair of mounting bars 500. It will be understood that in addition to the clips 402, any number of additional clips may be positioned on the mounting bar 204. As discussed above, each of the clips 402 includes a recess, for example, a recess 202, having a cross-section corresponding to that of the mounting bar 204. The mounting bar 204 is received in the recess 202 so that the clips 402 are movably positioned over the mounting bar 204. The clips 402 may be placed distal to the distalmost locking band, for example, the locking band 406a, which is coupled to the mounting bar 204 until the distal end of the endoscope 404. However, as would be understood by those skilled in the art, the clips 402 may be mounted proximally of one or both of the locking bands 406a, 406b so long as proximal ends of the locking bands 406a, 406b are shaped to facilitate the passage of the clips 402 therepast. For example, the proximal ends of the locking bands 406a, 406b may be tapered to allow the arms of the clips 404 to expand as they pass thereover. The mounting bar 204 may be made of a suitable biocompatible material that has a flexibility selected to permit the endoscope 404 to be maneuvered as desired.

As shown, a distal end 408 of the mounting bar 204 according to one embodiment is curved away from the locking bands 406a, 406b so that, when the mounting bar 204 is mounted on an endoscope 404 in a desired position, the distal end 408 extends distally beyond the distal end 405 of the endoscope 404. The curved distal end 408 aids in alignment of the clips 402a, 402b, 402c as they are pushed off the endoscope. In an exemplary embodiment, a curvature of the curved distal end 408 is selected to facilitate pointing the clips 100, 200, 300 over target portions of tissue. That is, the curvature of the curved distal end 408 moves the clips 100, 200, 300 out of the plane of the endoscope 404, thus facilitating visualization of the clips 100, 200, 300 as they are moved off the endoscope. It is noted that the curvature depicted in FIGS. 4-7 is exemplary only and any other curvature may be used without deviating from the scope of the invention. For example, the curvature may be formed as a slight tapering of the distal end of the mounting bar 204. In another embodiment of the invention (not shown), the mounting bar 204 may initially be provided in a straight configuration and may be formed of a flexible material. A manipulation wire (not shown) may extend from a proximal end accessible to a surgeon or other user to a distal end connected to a distal end of the mounting bar 204204. In an operative configuration, the surgeon may retract the manipulation wire (not shown) to curve the distal end of the mounting bar 204 by a desired degree prior to deployment of the clips 100, 200, 300. Specifically, the surgeon may retract the manipulation wire (not shown) by a first distance to cause a first curvature at the distal end 408 of the mounting bar 204 and by a second distance greater than a first distance to cause a second curvature greater than the first curvature.

During operation (FIG. 5), the mounting bar 204 is mounted over a distal portion of the endoscope 404 and secured over the endoscope 404 using the locking bands 406a, 406b with the clips 402 received on the mounting bar 204 over the endoscope 404 with the wire 416 extending from the pusher 410 around the wire track 412 into the endoscope channel 418. It should be understood that the mounting bar 204 is a linking mechanism coupling the clips 402 to the endoscope 404. According to the embodiments of the present disclosure, mounting bars 204 may be manufactured in any of a variety of dimensions to suit these mounting bars 204 for use with a variety of scopes such as bronchoscopes, cystoscope, etc. so that the clips 402 may be used to compress tissues of various body organs such as lungs, bladder, etc.

The cross-section of the combined distal portion of the endoscope 404 including the mounting bar 204, clips 402 and the pusher 410 is suitably dimensioned to facilitate smoothly advancing the combined system through a body lumen to a desired treatment site. For instance, the combined distal portion of the endoscope 404 may specially be sized and configured to pass through the esophagus to the stomach, etc.

The first and the second clip arms, such as the clip arms 104a, 104b, of each of the clips 402 is maintained in an open position by contact between the endoscope 404 on the which the mounting bar 204 is mounted and the inner surfaces, such as the inner surfaces 110, of the first and the second clip arms 104a, 104b. The engagement between the clip arms 104a, 104b and the endoscope 404 is such that the endoscope 404 holds the clips 402 while the endoscope 404 is being navigated through a patient's body.

At the treatment site, target tissue is at least partially drawn into the endoscope 404, e.g., by applying negative pressure through the endoscope channel 418, for example, using a suction pump. Once the tissue has been drawn into the distal end of the endoscope 404, actuation of a proximal end (not shown) of the wire 416 causes distal movement of the pusher 410 along the mounting bar 204, the distal movement advancing the clips 402 along the mounting bar 204 until a distalmost one of the clips 402 is moved distally beyond the distal end of the mounting bar 204 and the endoscope 404. Specifically, as the pusher 410 moves distally, the clips 402 are slid distally along the mounting bar 204 until a distalmost clip 402, for example, the clip 402a, moves distally beyond the distal end of the endoscope 404. At this point, as the arms 104a. 104b are no longer supported by the endoscope 404, they draw inward toward one another gripping the tissue that has been drawn into the endoscope 404. As the distalmost clip 402a moves distally past the distal end of the mounting bar 204, the clip 402a is released from the mounting bar 204 and is completely disconnected from the system 400 so that it may be left in place at the site of the clipped tissue.

The endoscope 404 may then be repositioned adjacent to a second target portion of tissue and the process may be repeated to deploy a second clip 402b at this site. The process may then be repeated as many times as desired until all the clips 402 have been deployed or until all the target tissue sites have been treated. When the last tissue site has been treated, the endoscope 404 is removed from the body. As would be understood by hose skilled in the art, any or all parts of the clip system 400 such as the clips 402 or the pusher 410 may be made of, or incorporate, a radiopaque material, so that these parts are visible using fluoroscopy or other forms of X-ray imaging. The clips 402 may be made of any suitable biocompatible material known in the art and may include biodegradable materials including, but not limited to poly (D,L-lactide-co-glycolide). As would be understood by those skilled in the art, if the clips 402 are not biodegradable, the clips may be left in place until the clips slough off through the body's natural healing processes. Alternatively, a separate procedure may be performed to remove the clips after a desired healing time has elapsed.

Although the system 400 has been explained with respect to an endoscope, it will be well understood by a person skilled in the art that the system may be incorporated or otherwise used with a catheter having any cross-section and a lumen.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A system for compressing body tissue, comprising:
   a mounting bar comprising a coupling structure, the coupling structure configured to mount the mounting bar on an endoscope so that the mounting bar extends along a distal end of the endoscope parallel to a longitudinal axis;
   a clip comprising a connection portion with first and second clip arms extending therefrom, the clip including a recess formed on an inner surface of the connection portion, the recess being shaped and sized to slidably receive the mounting bar with inner surfaces of the first and second clip arms being maintained in an open position by contact between the endoscope and the inner surfaces of the first and second clip arms; and
   a control member coupled to the clip to move the clip along the mounting bar until the clip moves distally beyond the distal end of the endoscope so that the first and second clip arms spring closed to grip tissue therebetween.

2. The system of claim 1, wherein a cross-sectional shape of the recess conforms to a cross-sectional shape of the mounting bar.

3. The system of claim 2, wherein the recess has one of a rectangular, oval, circular, T-shape, a shape having first and second walls extending into the connection portion at opposing angles and a third wall extending between the first and second walls, the third wall being one of planar and curved with a curvature corresponding to a curvature of the inner surface of the connecting member.

4. The system of claim 1, wherein the inner surfaces of the first and second clip arms form a portion of an arc of a circle to conform to a shape of an outer surface of the endoscope.

5. The system of claim 1, wherein the inner surface of the first clip arm comprises a surface treatment to enhance frictional engagement thereof with the endoscope, the surface treatment extending over at least a portion of the inner surface of the first clip arm.

6. The system of claim 1, wherein the first and second clip arms are biased to a closed configuration in which the first and second arms are moved radially inward toward a contacting configuration, the clip having a spring constant selected to maintain a frictional engagement with the endoscope.

7. The system of claim 6, wherein the first and second clip arms are held in a radially expanded configuration by the endoscope.

8. The system of claim 1, wherein a lower surface of the mounting bar is formed with a curvature conforming to a curvature of the endoscope.

9. The system of claim 1, wherein the recess comprises a shoulder preventing contact between the mounting bar and the endoscope.

10. The system of claim 1, wherein a thickness of the clip is greater at the first end than the second end to form a crescent shape.

11. The system of claim 1, wherein the clip includes a spring formed at the first ends, the spring including first and second extension arms to aid in grasping tissue between the first and second clip arms.

12. The system of claim 1, wherein the coupling structure includes a circular locking band connected to the mounting bar removably positionable over the distal end of the endoscope.

13. The system of claim 1, wherein the control member comprises:
   a pusher slidably connected to the mounting bar; and
   a wire extending from a first end connected to the pusher, through a channel formed in the mounting bar to extend into the endoscope, a second end of the wire accessible to a user to permit controlled deployment of the clip.

14. The system of claim 13, further comprising a wire track attached to the mounting bar and including a rail to guide the wire along a predefined path, the wire track positioned over a distal opening of the endoscope in an operative configuration.

15. The system of claim 1, further comprising a plurality of additional clips positioned on the mounting bar.

16. A device for compressing body tissue, comprising:
a clip comprising a connection portion with first and second clip arms extending therefrom, the clip comprising a recess formed on an inner surface of the connection portion, the recess being shaped and sized to slidably receive a mounting bar coupled to an outer surface of an endoscope with inner surfaces of the first and second clip arms maintained in an open position by contact between the endoscope and the inner surfaces of the first and second clip arms,
wherein the clip is slidable over the outer surface of the endoscope until the clip moves distally beyond the distal end of the endoscope so that the first and second clip arms spring closed to grip tissue therebetween.

17. The device of claim 16, wherein the first and second clip arms are biased toward a closed configuration in which the first and second arms are moved radially inward toward a gripping configuration.

\* \* \* \* \*